US006823211B2

(12) United States Patent
Simpson et al.

(10) Patent No.: US 6,823,211 B2
(45) Date of Patent: Nov. 23, 2004

(54) DEVICE FOR PREDICTION OF HUMAN OR MAMMALIAN LABOR

(75) Inventors: Nigel Alastair Buist Simpson, Leeds (GB); James Johnston Walker, Leeds (GB)

(73) Assignee: Jopejo Limited, Leeds (GB)

( * ) Notice: Subject to any disclaimer, the term of this patent is extended or adjusted under 35 U.S.C. 154(b) by 193 days.

(21) Appl. No.: 10/149,422

(22) PCT Filed: Dec. 20, 2000

(86) PCT No.: PCT/GB00/04880
§ 371 (c)(1),
(2), (4) Date: Jun. 21, 2002

(87) PCT Pub. No.: WO01/45555
PCT Pub. Date: Jun. 28, 2001

(65) Prior Publication Data
US 2002/0193701 A1 Dec. 19, 2002

(30) Foreign Application Priority Data
Dec. 21, 1999 (GB) .............................. 9930025

(51) Int. Cl.[7] .............................................. A61B 5/04
(52) U.S. Cl. ...................................... 600/546; 600/304
(58) Field of Search ................................ 600/304, 546, 600/588

(56) References Cited

U.S. PATENT DOCUMENTS

| | | | |
|---|---|---|---|
| 4,256,118 A | | 3/1981 | Nagel |
| 4,967,761 A | | 11/1990 | Nathanielsz |
| 5,373,852 A | | 12/1994 | Harrison et al. |
| 5,776,073 A | | 7/1998 | Garfield et al. |
| 6,421,558 B1 | * | 7/2002 | Huey et al. .................. 600/546 |

FOREIGN PATENT DOCUMENTS

| | | |
|---|---|---|
| WO | 9413202 | 6/1994 |
| WO | 9414373 | 7/1994 |
| WO | 9531932 | 11/1995 |
| WO | 9639931 | 12/1996 |
| WO | 9725922 | 7/1997 |

OTHER PUBLICATIONS

C. Marque, et al., Uterine EHG Processing For Obstetrical Monitoring, IEEE Transactions on Biomedical Engineering, vol. BME–33, No. 12, Dec. 1986, pp. 1182–1187.
C. Buhimischi, et al., Electrical Activity of the Human Uterus During Pregnancy as Recorded From the Abdominal Surface, Obstetrics & Gynecology, vol. 90, No. 1, Jul. 1997, pp. 102–111.
N.A.B. Simpson, et al., Changes in Uterine Electrical Activity Associated with Onset of Labour in Human Pregnancy, Journal of Physiology, vol. 507P. Jan. 1998, p. 68P.
N.A.B. Simpson, et al., Characteristics of the Electrohysterogram May Predict Uterine Preparedness For Labour, American Journal of Obstetrics and Gynecology, vol. 178, No. 1, Part 2, Feb. 1998, p. S91.

* cited by examiner

Primary Examiner—Eric F. Winakur
(74) Attorney, Agent, or Firm—Jacobson Holman PLLC

(57) ABSTRACT

A device for prediction of onset of labor comprises a portable assembly of a plurality of recording electrodes (3) and optionally a reference electrode (4), a means for data acquisition (1), a means for conversion of analogue to digitized data and a display (5) adapted to display this data in terms of one of a small number of discrete results indicative of the state of preparedness for labor, wherein each electrode (3) comprises a contact surface for application to a subject, and in particular to an abdominal and/or vaginal surface of a subject, the device further comprising data analyzing means (1) for analyzing the digitized data with reference to pre-recorded reference data and/or predetermined reference parameters. A method for prediction of onset of labor comprises applying the electrodes (3) to an abdominal and/or vaginal surface of a subject, collecting and analyzing the data, and displaying the result in terms of one of a small number of discrete results indicative of the state of preparedness for labor.

24 Claims, 3 Drawing Sheets

DEVICE FOR PREDICTION OF HUMAN OR MAMMALIAN LABOR

This is a nationalization of PCT/GB00/04880 filed Dec. 20, 2000 and published in English.

The present invention relates to a device for the prediction of the onset of labour in humans or animals, a method for predicting labour using the device and the use thereof. More specifically the invention relates to a device for predicting the onset of labour which may be premature, on time or delayed, a method thereof using the device, operated by the subject or another individual and the use thereof.

Measurement of uterine contractions to determine the state of pregnancy and diagnose real labour is well documented. For example U.S. Pat. No. 4,967,761 (Nathanielsz) discloses a method comprising sensing myometrial contractility, producing signals representing the sensed contractility, storing the signals and determining characteristic representative frequencies which are then classified as term or preterm labour. WO 94/13202 (Rosenberg) discloses a method and device as a diagnostic tool by means of assessing muscular contraction. Such clinical assessment by means of evaluating the mechanical activity in terms of strength, duration and frequency of palpated contractions do not however correlate with onset or progress of labour, and are liable to considerable inter-observer variation.

Measurement of electrical activity, electrohysterography, has been proposed as an alternative approach to the detection of labour. For example WO 94/14373 (Garfield) records signals from embedded electrodes, WO 95/31932 and WO 96/39931 (Garfield) disclose a method which stores data and compares activity and U.S. Pat. No. 5,373,852 (Harrison) uses radiotelemetric transmission for sensing pressure, temperature and electrical activity. WO 97/25922 (Rosenberg) discloses a further method for analysis of electromyographic data.

However such publications relate exclusively to clinical, usually intrusive techniques for data collection. Moreover, data analysis and/or diagnosis is generally also by complex methods requiring expert operation. These are therefore of limited application, inconvenient since they require the intervention of a clinician, and hence usually require the subject to attend a hospital, clinic or the like and are therefore limited in application since the likelihood of detecting abnormal pregnancies is low.

Moreover the disclosures all relate to methods for analysing data obtained by electrohysterography using various forms of frequency analysis which are limited and used for the diagnosis of contractile or true labour. The methods described, and in particular the analytical techniques employed, are not disclosed as predictive tools to determine the progress of the precontractile preparative phase of parturition prior to the onset of labour. Thus, the prior art discloses diagnostic tools which can give a measure as to whether a symptomatic patient is in labour only.

Accordingly there is a need for a device which non-intrusively predicts the onset of labour and/or which indicates the imminence of labour and which is suited for non clinical, i.e., home use. In particular, there is a desire for a device which can both be operated in a domiciliary environment and produce results which can be interpreted without the need for a clinician.

We have now surprisingly found that a device and method can be provided for non intrusive non clinical use which can enable the prediction of onset of labour and or indicate the imminence of labour and which can be operated by the subject or any observer without clinical knowledge, or specific expertise relating to the technique.

Since the device and method of the invention is predictive rather than merely diagnostic of labour it enables for the first time measures to be taken to provide medical assistance where necessary in the instance of premature labour, in advance of the event itself, thereby allowing for example preventative action, simplifying any remedial action and reducing loss of life or birth defects which might result from premature labour. The device and method also enable subjects to determine the expected onset of their labour with accuracy. This will help to avoid false alarms which are distressful and often dangerous for the subjects attempting to reach medical help, and are an undue burden on the medical services, but will also help to ensure that subjects remain within reasonable reach of medical assistance when onset of labour is close.

Accordingly in a first aspect of the invention there is provided a device for prediction of onset of labour comprising a portable assembly of a plurality of recording electrodes and optionally a reference electrode, a means for data acquisition, a means for conversion of analogue to digitised data and a display adapted to display this data in terms of one of a small number of discrete results indicative of the state of preparedness for labour, for example in terms of a positive or negative result indicating the preparedness for labour, wherein each electrode comprises a contact surface for application to a subject, and in particular to an abdominal and/or vaginal surface of a subject, the device further comprising data analysing means for analysing the digitised data with reference to pre-recorded reference data and/or predetermined reference parameters, the assembly being operatively associated in compact manner.

The device records uterine electrical activity, in particular by application to the abdominal or vaginal surface, in generally similar manner to that known in the art. That is to say, a plurality of recording electrodes for measuring action potential are provided which are applicable to an abdominal or vaginal surface of a patient under analysis; the analogue to digital convertor connected to the electrodes acts to convert electromyographic signals produced by the electrodes into digitised data indicative of the electromyographic signals and action potentials; and the digitised data is stored and analysed with reference to prerecorded reference data and/or predetermined reference parameters, the results being used to actuate a display adapted to display this data as indicating one of a small number of discrete conditions indicative of the measured uterine activity.

The invention differs from the prior art by exploiting the surprising result that analysis of uterine electrical activity can be used not merely to monitor the progress of, and/or diagnose active labour as in the prior art, but can be used to obtain an indication of uterine preparedness for labour in the initial phase of parturition before onset of active labour.

The display is adapted to work in conjunction with the pre-recorded reference data and/or pre-determined reference parameters to provide a simple display indicating one of a few discrete states of uterine preparedness for labour (for example a two-state model indicating a positive or negative result for preparedness; a three-state model indicating for example pre-parturition, early stage changes, and full preparedness etc.).

The present invention thus enables for the first time a prediction of the onset of labour and/or a monitoring of the pre-labour phase of parturition, as the uterus prepares for the contractile or labour phase of parturition. Moreover, the invention does this in a compact and portable manner, and by displaying only a small number of discrete results, provides a result which can be readily interpreted by a subject without the need for intervention by a clinician, and is thus particularly suited to home use.

The present invention provides highly reliable results based on the finding that certain parameters govern the production of uterine electrical signals. Specifically there is an increase in the number of intercell connections (gap junctions) which then facilitate the spread of electrical impulses from one part of the womb (uterus) to another, allowing for progressively synchronous and effective mechanical activity (contractions). These changes occur progressively throughout the pre-labour phase of parturition. We judge that the observed change in the rhythms governing electrical activity reflect these cellular changes.

This finding is highly significant in our ability to provide for the first time a display device, since the characterisation of signals into ranges is for the first time reliably facilitated. This characterisation of signals into ranges allows the provision of a simple display device, capable of displaying results which are readily understood by a non-specialised user, and which, in contrast to the prior art devices, do not require the analysis of a clinician to obtain a meaningful prognosis or diagnosis.

In particular, we are able to pre-record reference data and/or to pre-programme particular reference parameters which are characteristic of a small number of pre-defined pre-labour states indicating the progress of preparedness for contractile labour. For example, data is pre-recorded and/or parameters are pre-programmed which correspond to uterine electrical activity indicative of the pre-parturition state and uterine activity indicative of a state of full or near-fill full uterine preparedness for active contractile labour, and the display means are configured to display one or other state accordingly as a positive/negative result. Optionally, further data and/or parameters are stored representative of one or more intermediate states as the preparation phase of parturition has progressed to a greater or lesser extent. A comparison of changes in electrical activity against these referenced parameters can offer an indication of the imminence of full preparedness for labour.

The device thus offers for the first time a tool which is not merely diagnostic of active labour and/or a tool for analysing the progress of active labour, but is predictive of the onset of labour by enabling a diagnosis and monitoring to be made during the preparation phase of parturition. Moreover, the device achieves this objective in a compact and portable manner which is particularly suited for home use.

U.S. Pat. No. 4,256,118 (Nagel) for example has disclosed intrauterine pressure variation via electrohysterography as the governing parameter and is superseded by/further refined by the present invention.

The display of the invention is adapted to display the converted digitised data in terms of one of a small number of discrete results indicating the state of preparedness for labour. The digitised data indicative of uterine electrical activity is compared with suitable pre-recorded reference data and/or predetermined reference parameters by the data analyser and is characterised as being indicative of a state of preparedness corresponding to one of the said discrete results, and the display is then actuated to make such an indication.

In its simplest embodiment, the display may be configured to indicate a positive or negative result as to whether the uterus is substantially prepared for contractile labour. However, it is known that the first phase of parturition in which the uterus prepares for labour extends over a period of time, and we have now found that detectable electrical changes occur within the uterus over this time. Accordingly, the display means is preferably adapted to display the digitised and analysed data in terms of at least three discrete results (the pre-recorded reference data and/or predetermined reference parameters being set accordingly), the at least three results preferably including an indication of activity levels corresponding to the pre-parturition stage, an indication of near-full or full preparedness for labour, and at least one indication of an intermediate state of preparedness.

It is found that detectable changes can be obtained for many subjects at least two weeks before the onset of labour, and these detectable changes can therefore be used to effect such an intermediate reading. The device therefore displays negative/intermediate/positive results, which for practical purposes from the perspective of the subject could be thought to correspond to: labour distant (retest in a week or so)/labour likely in a week or two (retest daily, remain accessible to medical attention)/labour imminent (prepare for onset of labour, treat any symptoms as probable labour). The display means may include an alphanumeric display to display simple instructional or informational messages, in particular messages to this effect.

As is illustrated by this embodiment, the particular advantage of present invention is that the display means can give simply understandable results which do not require the intervention of a clinician and which offer the potential for significant reduction in both false alarms and unexpected premature labour producing complications because of inaccessibility of medical assistance.

Preferably the device detects spread of electrical impulse throughout the uterus, and classifies as a range, in the scale of 0–100% intercell connection within the uterus.

The device of the invention suitably comprises any means for operatively associating the assembly of components such as a casing, mounting, cassette, card, frame or the like. A mounting may be rigid or flexible, for example a flexible mounting may comprise an article of clothing such as a belt, patch or the like which may be conveniently worn by the subject for prolonged periods without inconvenience.

The device may be manually operated or may comprise means for intermittent operation allowing periodic inspection on a regular basis.

Activation may be manual or automated for example as a periodic activation using a timer control means, and/or as a manual activation such as through a power switch. The device preferably incorporates a portable power supply such as a rechargeable or non-rechargeable battery. Additionally or alternatively means are provided to connect the device to a mains power supply.

Display means may be auditory, visual or both and conveniently indicates a result without the need for the subject to interpret levels or the frequencies of activity, i.e., in the form of a set of illuminating lights, tactile patterns such as vibration or discrete auditory signal or alarm or an alphanumeric display to display simple messages. In a multi-state embodiment such as the preferred three-state embodiment, multi-coloured lights may be used, each colour indicating a different state of preparedness.

Comparison with pre-recorded data maybe with data programmed by a medical supervisor, for example enabling detection of a particular condition or pre-labour period or combinations thereof as alternative or co-operative settings. Alternatively the pre-recorded data may be acquired by the device in a programming mode by the subject in a non-labour and in particular a pre-parturition condition in simple manner.

Data acquisition and digitisation is suitably carried out by means of a microprocessor associated co-operatively with the electrodes using known techniques. Data analysis is by any suitable means and method associated with parameters related to change in electrical signals. In particular, the signals are analysed by performing a spectral analysis of power density of electromyographic potentials, and the analyser is adapted to perform such an analysis, for example by suitable programming.

A number of special analysis techniques can be considered. For example, WO 96/39931 (Garfield) concentrates in particular on the peak power frequency produced by such a spectral analysis. Garfield diagnoses and monitors labour based on shifts in this peak power frequency which can be expected once labour has started.

The present invention is concerned with an analysis of pre-labour uterine electrical activity to facilitate the prediction of onset of labour. Thus, in the preferred embodiment, analysis is by power spectral time averaging providing high:low frequency data, for example as disclosed by:

Marque C, Duchene J, Leclercq S, Panczer G S, Chaumont J (1986) Uterine EHG processing for obstetrical monitoring, IEEE Transactions on Biomedical Engineering 33: 1182–1187

Buhimischi C, Boyle M B, Garfield R E (1997) Electrical Activity of the human uterus during pregnancy as recorded from the abdominal surface. Obstet Gynecol 90: 102–111

Simpson N A B, Barker A, Wall O, Snowden S, Smye S, Walker J J (1998) Changes in uterine electrical activity associated with onset of labour in human pregnancy. Presented to The Physiological Society, London, January 1998, J. Physiol 507P:68P Simpson NAB, Snowden S, Barker A, Wall O, Smye S, Walker J J (1998) Characteristics of the electrohysterogram may predict uterine preparedness for labour. Presented at the 18$^{th}$ annual SPO meeting, Miami, January 1998. Am J Obstet Gynecol 178; 1(2):S91

Thus, the preferred frequency analysis method for analysing the signal comprises producing a power spectrum, and performing a load average ratio analysis of at least one low and one high frequency range. The analyser is adapted to perform such an analysis (e.g. by suitably programming). This load average ratio analysis will produce results which vary in a predictable and measurable manner as the preparation phase of parturition proceeds, and will thus enable ranges to be accurately characterised for reference purposes as required by the invention. The analyser may be adapted to perform load average ratio analysis of two or more frequency ranges, which may be discrete or abutting ranges, and which may cover certain parts or substantially all of the practical range of frequencies.

A suitable frequency range is up to 5 Hz, preferably in a low and a high band within a 0–5 Hz range, for example 0.2–0.45 Hz, and 0.8–3.0 Hz.

The total power, measured as the area under the above within the range of frequencies is also significant.

Of all the electrical changes which occur during the preparatory phase of parturition, frequency shifts are particularly marked. This analytical technique enables frequency shifts corresponding to increased intercellular electrical activity to be identified particularly effectively, and characteristic ranges determined, to assist in the provision of pre-recorded reference data and/or pre-determined reference parameters for the device of the invention.

An analysis based on the load average ratio is believed to provide a particularly effective method of interpreting the variation between low and high frequency bursts of electrical activity which appears to occur during the preparation phase of parturition as the number of gap junctions increases as the uterus prepares for contractile labour. The statistical analysis technique of the preferred embodiment is thus particularly effective in the context of the present invention in providing a device which effectively predicts the onset of labour, when compared with statistical analysis techniques suggested for example in WO 96/39931.

Data analyser and display means operating this preferred embodiment of the invention thus comprise an analyser such as a microprocessor or filter adapted, for example suitably programmed, to categorise data having high:low frequencies in at least two ranges, to perform an analysis of power load averages between the at least two ranges and to provide a given signal to the display in response to a given ratio of power load averages between the at least two ranges.

The present invention thus provides for the first time means for displaying frequency-analysed electrohysterographic data in form of a small number of discrete results such as a positive or negative result and optionally further one or more intermediate results, in particular results which indicate not merely a diagnosis of labour, but a prediction of its onset.

In a further aspect of the invention there is provided a method for predicting onset of labour comprising applying a device as hereinbefore defined to the skin of a subject in the uterine region, activating the device for a sufficient period to record electrical activity and obtaining a displayed result comprising one of a small number of discrete results indicative of a state of uterine preparedness for labour, for example a positive or negative result, and optionally additionally one or more intermediate results as above described.

In particular, the method comprises applying potential measuring electrodes to an abdominal or vaginal surface of a patient in the uterine region, activating the device for a sufficient period to record electrical activity, acquiring data corresponding to the electrical activity, converting acquired analogue to digitised data, analysing the data to produce an analysis of uterine activity with reference to pre-recorded reference data and/or pre-determined reference parameters, and as a result of said analysis causing a result to be displayed which comprises one of a small number of discrete results corresponding to the analysed uterine activity and indicative of a state of uterine preparedness for labour.

Preferably the device and method detect spread of electrical impulse throughout the uterus, and classifies as a range or series of ranges, in the scale of 0–100% intercell connection within the uterus.

Preferably, the method involves analysing the data by a power frequency analysis technique, and in particular the analysis comprises determining a load average ratio between at least one high frequency range and at least one low frequency range, and categorising the result to correspond to one of the said discrete states by comparison with the reference data and/or reference parameters.

Application of the device may be temporary or permanent, i.e., the device may be applied periodically by the subject or may be worn as part of thick clothing.

The method may comprise a preliminary non-labour programming stage to acquire non-labour data. Alternatively the method may be operated with a pre-programmed device.

Further features of the method will be apparent from the aforegoing description.

In a further aspect of the invention there is provided the use of a device or method as hereinbefore defined for predicting premature, on time or delayed labour in advance of physically detectable or observable contractual activity.

The use of the invention has particular advantages in facilitating preventative and remedial clinical action, reducing the instance of death or abnormal birth and effects on mother and child and moreover is convenient in minimising stress to the subject and false alarms to clinical staff.

The use may be human or animal use. In each case the device may be used for humans and animals in remote regions enabling them to remain in their natural environment throughout the duration of pre-labour pregnancy and to detect prediction of labour onset for a suitable period enabling travel to assistance.

Use of the device may be use within the home or in transit, during a subject's normal daily activities in public, in hospitals, clinics and the like. It is a particular advantage that the use is simple, convenient and the device may be operated by skilled or unskilled personnel, by the subject or any other person.

In a further aspect of the invention there is provided a device programmed to predict the onset of labour as hereinbefore defined. Preferably the device comprises a signal capture/analysis/display means programmed to perform the sequence of activities defined in FIG. 1.

The invention is now illustrated in non-limiting manner with reference to the Figures and examples wherein.

Figure 1A:
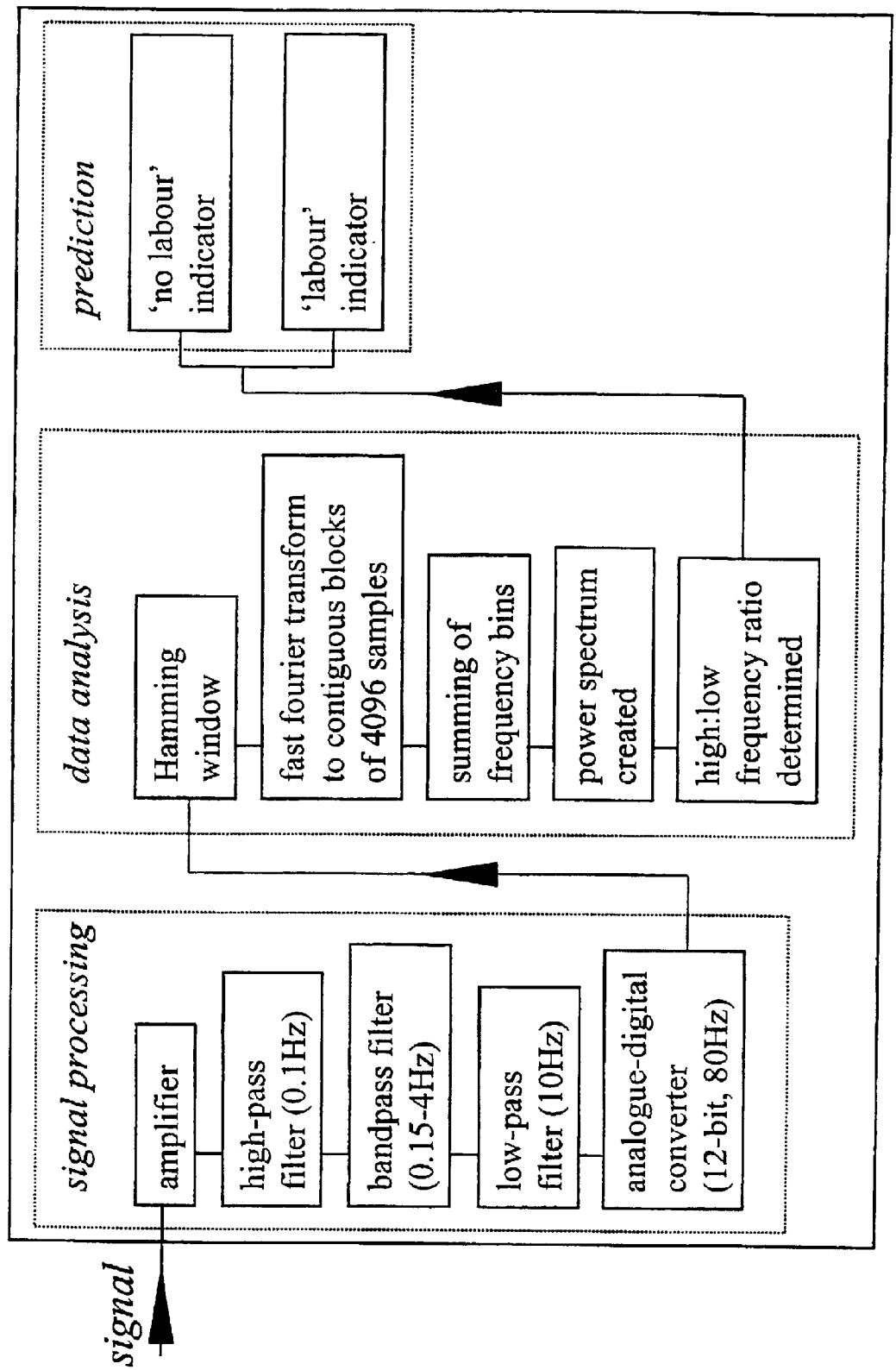
FIGS. 1a and 1b illustrate the mechanism of the signal capture/analysis/display of two examples of means according to the invention.
Figure 1B:
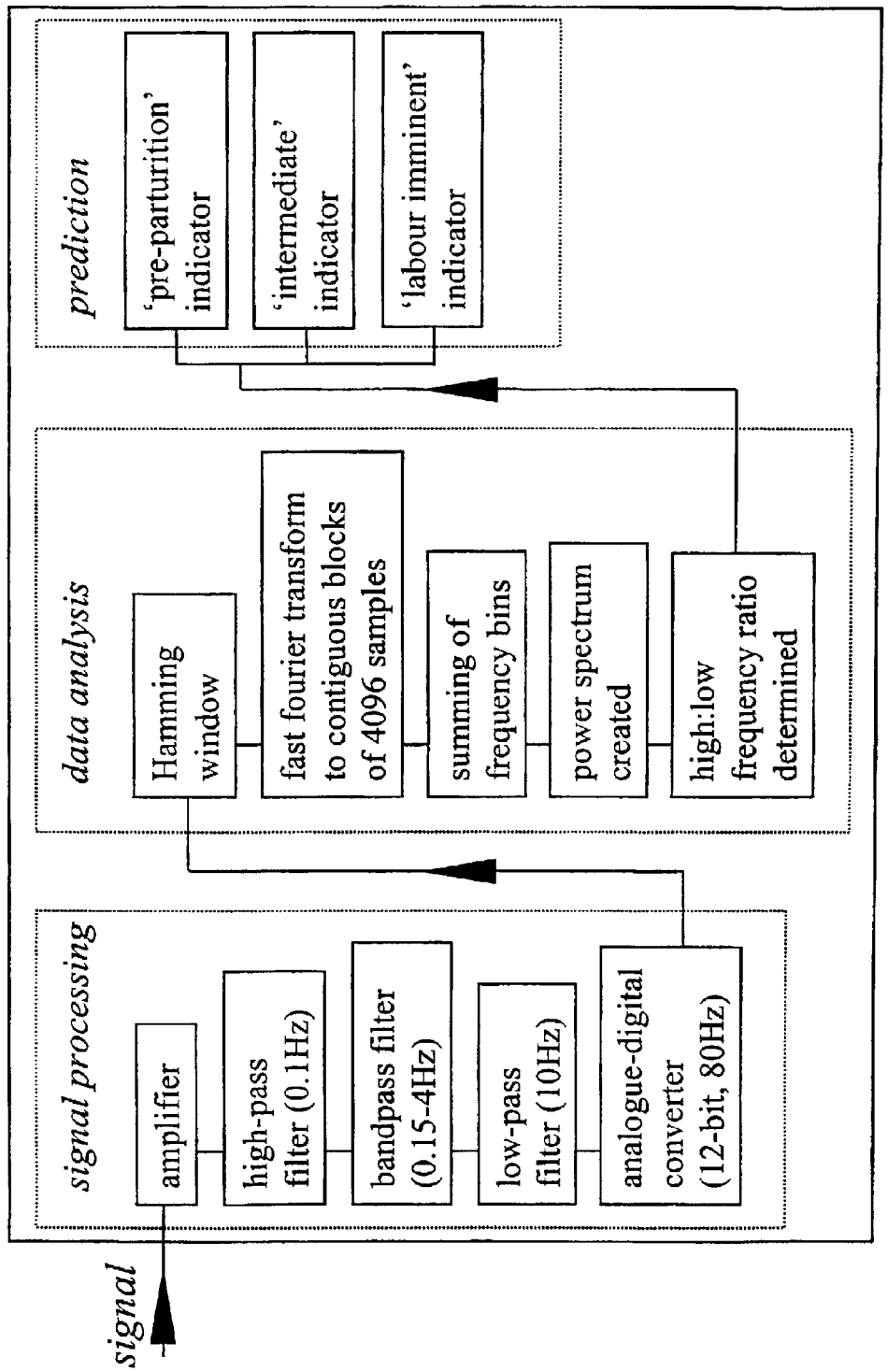

In FIG. 1 is illustrated the sequence of activities performed by the device programmed according to the invention, comprising in a first stage, signal processing, in a second stage data analysis and in a third stage, prediction of result. In FIG. 1a a simple two stage display phase is illustrated. In FIG. 1b the preferred three stage (pre-parturition, preparative, labour imminent) display phase is illustrated.

Figure 2:
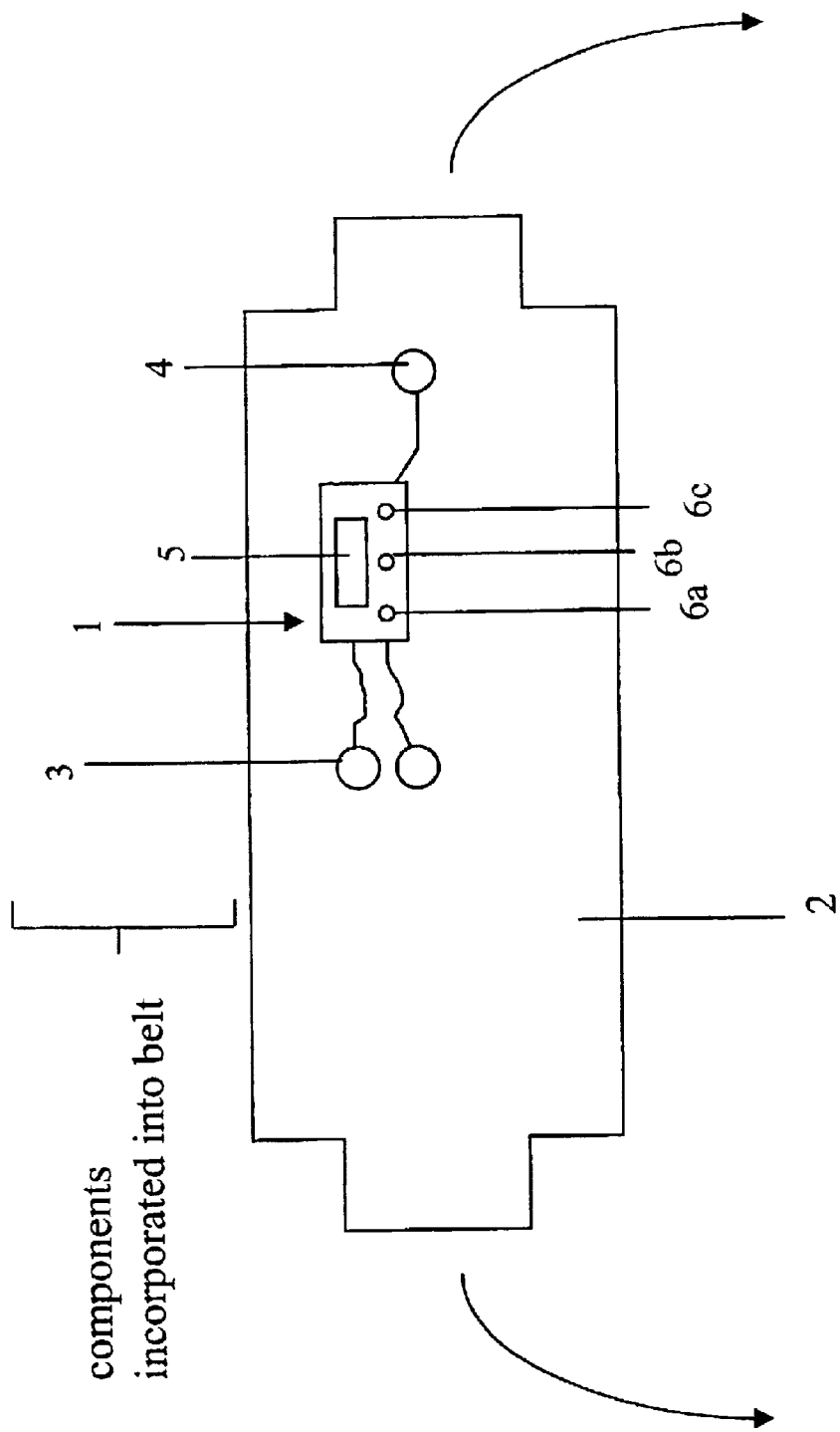
FIG. 2 illustrates an embodiment of the invention in the form of a belt/corset worn device.

In FIG. 2, the capture/analysis/display device (1) programmed according to FIG. 1 is mounted on belt/corset (2) connected to recording electrodes (3) and reference electrode (4).

The device (1) suitably comprises coloured lights (6a, 6b, 6c) indicative of discrete results states. In the preferred embodiment, three discrete results states are envisaged, generally representing pre-parturition, early to mid uterine preparedness, and near-labour. For example, green, amber and red lights may be used. An LCD panel (5) is pre-programmed to display simple alphanumeric information. This may include, for example, approximate time to labour and/or instructions on recommended duration before a re-test is carried out. In this way, the device is adapted for simple home use by a subject without acquiring any special medical knowledge, to give both reassurance when labour is distant, early warning when labour is not so distant, and a full alert when labour is imminent.

The device also comprises an on/off switch (7) and a battery panel.

Further aspects of the invention with be apparent from the foregoing.

EXAMPLE 1

The device of FIG. 2 programmed according to FIG. 1b to perform a load average ratio analysis of a power frequency spectrum of the captured signals within a 0.3–0.8 Hz high band frequency, 0.8–3 Hz low band frequency is worn daily by a subject over a 4 week period up to her expected date for giving birth. Daily inspection is by means of switching the device on at the switch (7) for a period sufficient for signal capture, analysis and display. Inspection initially indicates no result, for example a green light (6a).

The first positive result may be recorded up to two weeks prior to onset of mechanical contractions. Pre-programmed data and/or pre-programmed reference parameters ensure that this can be interpreted by the device, and displayed as an intermediate result. For example, an amber light (6b) is illuminated, a display that labour may be expected within such a time scale, and instruction to re-test daily etc. may be displayed at the LCD display (5).

As the preparation phase of parturition proceeds as the uterus prepares for labour, the relative proportions of low and high frequency activity signals, and consequently the analysed load average ratio, will be expected to change further. Pre-programmed data and/or parameters are also stored representative of full or near-full preparedness for labour. When the data captured corresponds to these, a full positive result is given and serves to predict onset in the ensuing couple of days.

Both the intermediate and the full positive result are effected by the development of intercell connections facilitating spread of electrical impulses across the womb. The detection takes place on reaching a threshold level of electrical impulse detection corresponding to the state of intercell connections from 0 to 100% complete. In the embodiment corresponding to the display system of FIG. 1b, two such thresholds are provided, corresponding to the early stage and the near-complete stage.

What is claimed is:

1. A device for prediction of onset of labour comprising a portable assembly of a plurality of recording electrodes, a means for data acquisition, a means for conversion of analogue to digitised data, and a display means for displaying this data in terms of one of a small number of discrete results indicative of the state of preparedness for labour, each electrode having a contact surface for application to a subject, the device further comprising data analysing means for analysing the digitised data with reference to prerecorded reference data and/or predetermined reference parameters, said data analysing means being adapted to analyse digitised data by performing a spectral analysis of power density of electromyo-graphic potentials, and also being adapted to produce a power spectrum, and perform a load average ratio analysis of at least one low and one high frequency range.

2. A device as claimed in claim 1 wherein the data analysing means is adapted to categorise data having high:low frequencies in at least two ranges, to perform an analysis of power load averages between the at least two ranges and to provide a given signal to the display means in response to a given ratio of power load averages between the at least two ranges.

3. A device as claimed in claim 1 wherein the data analysing means is adapted to categorise data in a low and a high band frequency within a 0–5 Hz range.

4. A device as claimed in claim 1 wherein the data analyser analysing means is adapted to make a comparison of changes in uterine electrical activity occurring progressively through the pre-labour phase of parturition against suitable reference parameters to determine an indication of imminence of preparedness for labour.

5. A device as claimed in claim 4 wherein data is pre-recorded and/or parameters are pre-programed which provide reference parameters against which the said progressive changes may be compared to identify uterine electrical activity indicative of the pre-parturition state and uterine activity indicative of a state of full or near-full uterine preparedness for active contractile labour, and the display means is configured to display one or other state accordingly as a positive/negative result.

6. A device as claimed in claim 5 wherein the display means is configured to indicate at least a positive or negative result as to whether the uterus is substantially prepared for contractile labour.

7. A device as claimed in claim 4 wherein data is prerecorded and/or parameters are pre-programmed which provide reference parameters against which the said progressive changes may be compared to identify uterine electrical activity indicative of the pre-parturition state and uterine activity indicative of a state of full or near-full uterine preparedness for active contractile labour and uterine activity indicative of at least one intermediate state as the preparation phase of parturition has progressed to a greater or lesser extent and the display means are configured to display such states accordingly.

8. A device as claimed in claim 7 wherein the display means is adapted to display the digitised and analysed data in terms of at least three discrete results, the at least three results including an indication of activity levels corresponding to the pre-parturition stage, an indication of near-full or full preparedness for labour, and at least one indication of an intermediate state of preparedness.

9. A device as claimed in claim 8 wherein the display means is adapted to provide a three-stage indication indicating respectively the pre-parturition stage, substantially full preparedness for labour, and an intermediate state of preparedness.

10. A device as claimed in claim 1 further comprising means for operatively associating the assembly of components.

11. A device as claimed in claim 10 comprising flexible mounting means serving to operatively associate the assembly of components.

12. A device as claimed in claim 11 wherein the flexible mounting means includes an article of clothing.

13. A device as claimed in claim 1 comprising means for actuation for intermittent operation.

14. A device as claimed in claim 1 comprising auditory display means.

15. A device as claimed in claim 1 comprising visual display means.

16. A device as claimed in claim 15 wherein the display means include multi-coloured lights, each colour indicating a different state of preparedness for labour.

17. A device as claimed in claim 1 further comprising a reference electrode.

18. A device as claimed in claim 1 comprising a microprocessor associated co-operatively with the electrodes adapted to carry out data acquisition and digitisation.

19. A method for predicting onset of labour using a device having a portable assembly of a plurality of recording electrodes, a means for data acquisition, a means for conversion of analogue to digitised data and a display adapted to display this data in terms of one of a small number of discrete results indicative of the state of preparedness for labour, each electrode having a contact surface for application to a subject, the device further comprising data analysing means for analysing the digitised data with reference to prerecorded reference data and/or predetermined reference parameters, said method comprising the steps of applying the device to the skin of a subject in the uterine region, activating the device for a sufficient period to record electrical activity and obtaining a displayed result comprising one of a small number of discrete results indicative of a state of uterine preparedness for labour, analysing the data by a power frequency analysis technique, determining a load average ratio between at least one high frequency range and at least one low frequency range, and categorising the result to correspond to one of the said discrete states by comparison with the reference data and/or reference parameters, and displaying the result accordingly.

20. The method of claim 19 comprising the steps of applying potential measuring electrodes to an abdominal surface of a patient in the uterine region, activating the device for a sufficient period to record electrical activity, acquiring data corresponding to the electrical activity, converting acquired analogue to digitised data, analysing the data to produce an analysis of uterine activity with reference to pre-recorded reference data and/or pre-determined reference parameters, and as a result of said analysis causing a result to be displayed which comprises one of a small number of discrete results corresponding to the analysed uterine activity and indicative of a state of uterine preparedness for labour.

21. The method of claim 19 comprising the step of analysing the data by making a comparison of changes in uterine electrical activity occurring progressively through the pre-labour phase of parturition against suitable reference parameters to determine an indication of imminence of preparedness for labour.

22. A device for prediction of onset of labour comprising a portable assembly of a plurality of recording electrodes, a means for data acquisition, a means for conversion of analogue to digitised data, and a display means for displaying this data in terms of one of a small number of discrete results indicative of the state of preparedness for labour, each electrode having a contact surface for application to a subject, the device further comprising data analysing means for analysing the digitised data with reference to prerecorded reference data and/or predetermined reference parameters, said data analysing means being adapted to make a comparison of changes in uterine electrical activity occurring progressively through the pre-labour phase of parturition against suitable reference parameters to determine an indication of imminence of preparedness for labour, wherein data is prerecorded and/or parameters are pre-programmed which provide reference parameters against which the said progressive changes may be compared to identify uterine electrical activity indicative of the pre-parturition state and uterine activity indicative of a state of full or near-full uterine preparedness for active contractile labour and uterine activity indicative of at least one intermediate state as the preparation phase of parturition has progressed to a greater or lesser extent and the display means are configured to display such states accordingly.

23. A device as claimed in claim 22 wherein the display means is adapted to display the digitised and analysed data in terms of at least three discrete results, the at least three results including an indication of activity levels corresponding to the pre-parturition stage, an indication of near-full or full preparedness for labour, and at least one indication of an intermediate state of preparedness.

24. A device as claimed in claim 23 wherein the display means is adapted to provide a three-stage indication indicating respectively the pre-parturition stage, substantially full preparedness for labour, and an intermediate state of preparedness.

* * * * *